(12) United States Patent
Petty

(10) Patent No.: US 8,216,849 B2
(45) Date of Patent: *Jul. 10, 2012

(54) COLORIMETRIC TEST FOR BRAKE SYSTEM CORROSION

(76) Inventor: Jon A. Petty, Loa, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/236,469

(22) Filed: Sep. 19, 2011

(65) Prior Publication Data

US 2012/0009684 A1    Jan. 12, 2012

Related U.S. Application Data

(63) Continuation of application No. 12/264,003, filed on Nov. 3, 2008, now Pat. No. 8,021,890.

(51) Int. Cl.
*G01N 21/77* (2006.01)
*G01N 33/20* (2006.01)
*G01L 5/28* (2006.01)

(52) U.S. Cl. ............ 436/84; 436/73; 436/164; 436/169; 422/400; 422/420; 73/39; 73/61.42; 73/61.43; 73/121

(58) Field of Classification Search ............... 436/73, 436/84, 164, 166, 169; 422/400, 420, 430; 73/39, 53.01, 61.41, 61.42, 61.43, 121
See application file for complete search history.

(56) References Cited

U.S. PATENT DOCUMENTS

| | | |
|---|---|---|
| 5,278,075 A | 1/1994 | Stone |
| 5,856,199 A | 1/1999 | Kreiser et al. |
| 6,043,096 A | 3/2000 | Evtodienko et al. |
| 6,651,487 B1 | 11/2003 | Petty |
| 6,691,562 B2 | 2/2004 | Petty |
| 6,821,786 B2 | 11/2004 | Rupp |
| 7,682,834 B1 * | 3/2010 | Petty ............... 436/169 |
| 8,021,890 B2 * | 9/2011 | Petty ............... 436/169 |
| 2008/0206874 A1 | 8/2008 | Manka |

* cited by examiner

*Primary Examiner* — Maureen Wallenhorst
(74) *Attorney, Agent, or Firm* — Quarles & Brady LLP; Gavin J. Milczarek-Desai

(57) ABSTRACT

A method and kit for determining a concentration of iron in brake fluid when contacting a colorimetric reagent such that a color results. The level of iron can be used to determine the amount of active corrosion within a brake system and determine if special service procedures are required.

8 Claims, 2 Drawing Sheets

COLORIMETRIC TEST FOR BRAKE SYSTEM CORROSION

CROSS REFERENCE TO RELATED APPLICATION

This application is a continuation of U.S. patent application Ser. No. 12/264,003, filed on Nov. 3, 2008, now U.S. Pat. No. 8,021,890, issued on Sep. 20, 2011.

BACKGROUND OF THE INVENTION

Description of the Related Art

Brake fluid tests have been in use for years to predict corrosion, to detect the presence of copper in the brake system, and to detect other problems with brake fluid. Most conventional brake fluid tests currently used are copper-detecting brake fluid test strips. Other conventional brake fluid testing methods utilize moisture test strips and boiling point analyzers. The main problem with conventional brake fluid tests is that they can not determine whether active corrosion of iron components is already taking place in the brake system. Although copper-detecting brake fluid test strips can accurately predict when corrosion may occur, it cannot directly measure active corrosion of iron components in the brake system.

Conventional copper-detecting brake fluid tests could benefit from another testing parameter besides copper to help determine when brake fluid can no longer perform its design function and comply with the Motorist Assurance Program (MAP) guidelines for brake fluid replacement. Part of the MAP guidelines require that brake fluid be replaced when the corrosion inhibitors are depleted and can no longer protect the brake system from corrosion.

Current technology is unable to measure the extent of iron corrosion in a vehicle to help determine if further inspection of brake system components is required, to determine whether a vehicle is a candidate for basic brake system service, or to determine if a more involved and expensive service is required. In addition, current technology is unable to estimate a risk factor associated with a vehicle brake system.

Conventional brake fluid testing methods can also be expensive. In addition, the amount of time to test and analyze the results of a conventional brake fluid testing method can be a lengthy process, requiring at least two weeks time before the results can be returned. For example, to accurately determine whether dissolved iron is present in the brake fluid in a vehicle brake system, a sample of brake fluid must be sent to a testing laboratory for inductively coupled plasma spectroscopy (ICP) testing. This type of laboratory testing is not practical for a service facility to use during regular vehicle inspection procedures. Currently, there is no colorimetric test to identify iron levels and corrosion risk in brake fluid that uses an "in the field" test to determine the corrosion level of the vehicle brake system and without having to withdraw a sample of the brake fluid and send it to a laboratory for analysis.

SUMMARY OF THE INVENTION

The invention relates to a method, apparatus and test kit for determining a concentration of iron in a brake fluid quickly and in a cost-efficient manner. Another objective of this invention is a method, apparatus and test kit for determining the level of both $FE^{+2}$ and $FE^{+3}$ dissolved iron ions in a hydraulic brake system.

In an embodiment of the invention, a method is provided for visually locating damaged brake system components from active iron corrosion by testing specific locations in the brake system. Another embodiment of the invention involves a method, apparatus and test kit using for visually determining the level of brake system service required and assessing a possible risk factor or risk scale for the current condition of the brake system based on a concentration of iron in a brake fluid.

The invention further provides a colorimetric test to identify iron levels and corrosion risk in brake fluid that complies with existing guideline for brake fluid replacement, such as the Motorist Assurance Program (MAP) uniform inspection and communication guidelines for brake fluid replacement, which requires brake fluid replacement when the corrosion inhibitors are depleted. Such depletion is inferable from the presence of iron ions in the brake fluid.

In its preferred embodiment, the present invention comprises a colorimetric reagent that contacts a brake fluid, resulting in a color that varies with the concentration of iron in the brake fluid. An automated embodiment of the invention includes an electronic color detector to automatically determine the results of the test by inserting the colorimetric reagent into the electronic color tester after making contact with the brake fluid to automatically determine the iron level.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

This invention is described in preferred embodiments in the following description with reference to the Figures, in which like numbers represent the same or similar elements.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Applicant's invention comprises a colorimetric reagent that produces a color that varies with the concentration of iron present when said colorimetric reagent makes contact with a brake fluid. New brake fluid has relatively low iron levels, usually less than 6 ppm iron, which can slightly vary depending on the storage container the manufacturer uses. Empirical testing has demonstrated that vehicles with 50-100 parts per million (ppm) iron are experiencing the beginning of active iron corrosion, and, as those levels rise above 100 ppm, the amount of corrosion and pitting of iron component increases.

Corrosion and pitting of iron components can cause component failure and seal damage, resulting in complete or partial brake failure. Empirical testing has demonstrated that higher iron levels are found nearest the brake component experiencing active corrosion. Conventional brake fluid testing methods are not suitable for determining the amount of iron present in brake fluid when testing a vehicular brake fluid system. For example, a vehicle with a copper level above 200 ppm, indicates that there is a possibility that corrosion exists, but the conventional testing methods have no way to measure the level of iron corrosion.

Figure 1:
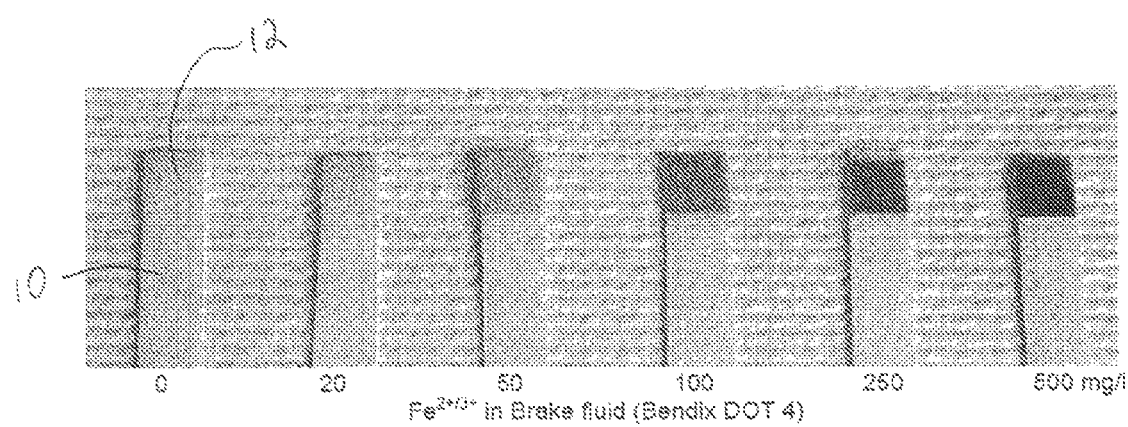
FIG. 1 shows the results tests for Iron (Fe+2 and Fe+3) concentrations in brake fluid according to the invention.

Referring to FIG. 1, dip test strips 10 having colormetric reagent 12 disposed thereon are diped into a sample of brake fluid for one second. The colormetric reagent is 2,2'-bipyridine. After shaking off excess fluid and waiting approximately 3 minutes, the strips show a red coloration that increases in intensity as the concentration of iron increases.

The colorimetric reagent may further contain an ingredient that reduces trivalent iron to bivalent iron, such a particular reagent may be more sensitive to this type of ion. In certain embodiments, the color reaction causes a gradual change from white to red. In one embodiment, the presence of a red color reaction from the colorimetric reagent can be used as an indication of active iron corrosion within the brake system. A bright red color, indicating 300 to 500 ppm iron, is an obvious sign of accelerated active brake system component iron corrosion.

Figure 2:
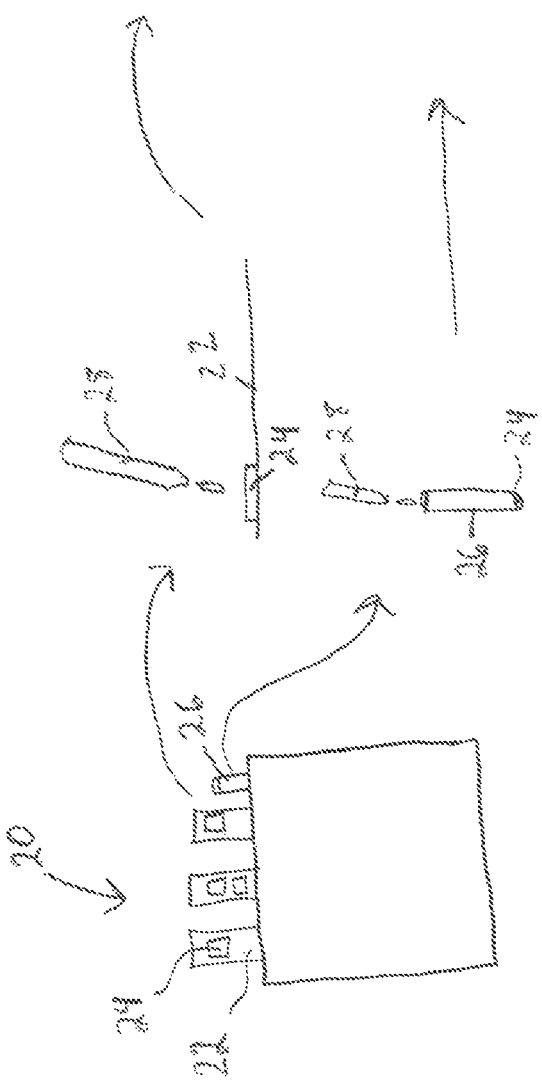
FIG. 2 is a schematic illustration of a kit embodiment of the invention.

Referring now to FIG. 2, a kit 20 of the invention includes a plurality of substrates (e.g., strips 22 and/or tubes 26) upon or within which colorimetric reagent 24 is disposed. A small sample of brake fluid 28 is dispensed from a dropper onto strip 22 or within tube 26, which may have the colorimetric reagent 24 already disposed within or added separately. Thus, brake fluid sample 28 contacts the colorimetric reagent and may be read manually for color content or with the aid of color testing machines. For example, a strip reading spectraphotometer 30 or tube reading spectraphotometer 32 may be employed to read the resulting color and provide a reading that correlates with the presence of an iron ion in the brake fluid. Of course, the colorimetric reagent may be disposed upon or within materials that are rigid, flexible and of various styles, shapes and sizes.

In certain embodiments, the test strip includes multiple reaction "zones" for different brake fluid tests testing the presence of active corrosive metal. Active corrosive metals can include iron, copper, zinc, or a combination thereof. In another embodiment, the brake fluid iron test may be performed with fluid from anywhere in the vehicle hydraulics system where access to brake fluid is available, such as at the bleeder screws located at each wheel at various anti-lock brakes (ABS) bleeder screw locations. If a high iron level is detected, i.e., 100 ppm or higher, additional testing may be required at various locations in the brake system in an attempt to identify the location of active corrosion.

While the preferred embodiments of the present invention have been illustrated in detail, it should be apparent that modifications and adaptations to those embodiments may occur to one skilled in the art without departing from the scope of the present invention.

What is claimed is:

1. A method for identifying a location of active corrosion in a metal brake component of a brake system through assessing a concentration of iron in brake fluid, comprising the steps of:
    (a) contacting a colorimetric reagent and a brake fluid sample located nearest to a first brake component at a first location in the brake system, wherein said colorimetric reagent reacts to produce a color indicating the presence of iron in said brake fluid sample, and
    (b) observing and comparing said color with a standard indicating an iron concentration of about 50 parts per million or greater, wherein if said color matches said standard indicating an iron level of about 50 parts per million or greater, additional testing of said first brake component at said first location in the brake system is performed in order to identify and confirm active corrosion of said first brake component.

2. The method of claim 1, wherein said colorimetric reagent contains an ingredient that reduces trivalent iron to bivalent iron.

3. The method of claim 1, wherein said colorimetric reagent comprises 2,2'-bipyridine.

4. The method of claim 1, wherein said color varies in intensity with the concentration of iron.

5. The method of claim 1, wherein said colorimetric reagent is affixed to a strip or dipstick.

6. The method of claim 5, wherein the strip or dipstick includes multiple colorimetric reagents for different brake fluid tests, wherein each of said reagents test for the presence of iron, copper, or zinc.

7. The method of claim 1, further comprising the step of analyzing said colorimetric reagent in an electronic color tester in step (b).

8. The method of claim 1, further comprising comparing said color with a standard indicating an iron concentration of about 100 parts per million or greater, wherein if said color matches said standard indicating an iron level of about 100 parts per million or greater, additional testing is performed on a brake fluid sample located nearest to a second brake component at another second location in the brake system in an attempt to identify a location of active corrosion.

* * * * *